United States Patent
Flaction et al.

(10) Patent No.: US 8,840,569 B2
(45) Date of Patent: Sep. 23, 2014

(54) METHOD AND DEVICE FOR ASSESSING MUSCULAR CAPACITIES OF ATHLETES USING SHORT TESTS

(75) Inventors: Patrick Flaction, Chandolin-près-Savièse (CH); Manu Praz, Baar (CH)

(73) Assignee: Myotest SA, Sion (CH)

( * ) Notice: Subject to any disclaimer, the term of this patent is extended or adjusted under 35 U.S.C. 154(b) by 183 days.

(21) Appl. No.: 12/209,044

(22) Filed: Sep. 11, 2008

(65) Prior Publication Data

US 2009/0069722 A1    Mar. 12, 2009

Related U.S. Application Data

(63) Continuation of application No. PCT/EP2007/052413, filed on Mar. 14, 2007.

(30) Foreign Application Priority Data

Mar. 17, 2006  (EP) ..................................... 06111352

(51) Int. Cl.
  *A61B 5/103*  (2006.01)
  *A61B 5/117*  (2006.01)

(52) U.S. Cl.
  USPC ............ 600/587; 600/595; 340/573.1; 482/8; 482/9; 702/141; 702/142

(58) Field of Classification Search
  USPC .............. 600/552–553, 587, 595; 606/46, 49; 340/573.1; 482/8–9; 702/141–142
  See application file for complete search history.

(56) References Cited

U.S. PATENT DOCUMENTS

| | | | |
|---|---|---|---|
| 4,699,379 A * | 10/1987 | Chateau et al. ................ 473/59 |
| 4,824,103 A * | 4/1989 | Smidt ............................ 482/9 |
| 5,056,783 A | 10/1991 | Matcovich et al. |
| 5,184,295 A | 2/1993 | Mann |
| 5,474,083 A | 12/1995 | Church et al. |
| 5,476,103 A * | 12/1995 | Nahsner ....................... 600/595 |
| 5,788,655 A | 8/1998 | Yoshimura et al. |
| 5,838,638 A * | 11/1998 | Tipton et al. .................. 368/10 |
| 6,148,280 A | 11/2000 | Kramer |
| 6,160,478 A * | 12/2000 | Jacobsen et al. ......... 340/539.12 |
| 6,167,356 A * | 12/2000 | Squadron et al. ............. 702/166 |
| 6,231,481 B1 * | 5/2001 | Brock ............................ 482/8 |
| 6,234,975 B1 * | 5/2001 | McLeod et al. ............... 600/552 |
| 6,389,894 B1 * | 5/2002 | Calame ...................... 73/379.01 |
| 6,397,151 B1 | 5/2002 | Yamagishi et al. |

(Continued)

FOREIGN PATENT DOCUMENTS

| | | |
|---|---|---|
| CN | 2930773 Y | 8/2007 |
| DE | 4426302 | 2/1996 |

(Continued)

*Primary Examiner* — Rene Towa
(74) *Attorney, Agent, or Firm* — Blank Rome LLP

(57) ABSTRACT

Device (1) for measuring muscular capacity, comprising:
  removable fastening means (12) for fastening the device to the athlete or to the moved weight (3; 2);
  autonomous electrical power supply means (15);
  a display (11);
  a three-axis accelerometer (14) for delivering a sequence of accelerations (a(t)) along the axis of movement of the weight, said sequence comprising at least 100 measurements per second over a duration between 1 and 10 seconds; and
  data processing means (16) for determining, at the end of the test, on the basis of said sequence of accelerations, at least one quantity representative of the muscular capacity of the athlete and for displaying this quantity on said display (11).

25 Claims, 7 Drawing Sheets

(56) References Cited

U.S. PATENT DOCUMENTS

| | | |
|---|---|---|
| 6,430,997 B1 * | 8/2002 | French et al. .............. 73/379.04 |
| 6,635,013 B2 | 10/2003 | Pfeffer |
| 2002/0028730 A1 | 3/2002 | Kaufman |
| 2002/0170193 A1 * | 11/2002 | Townsend et al. .............. 33/512 |
| 2004/0134274 A1 | 7/2004 | Hoggan et al. |
| 2005/0075586 A1 * | 4/2005 | Jamsen ........................ 600/595 |
| 2005/0172311 A1 * | 8/2005 | Hjelt et al. ...................... 725/10 |
| 2006/0191335 A1 | 8/2006 | Nose et al. |
| 2007/0027369 A1 * | 2/2007 | Pagnacco et al. ............. 600/301 |
| 2007/0042866 A1 * | 2/2007 | Skilken et al. .................... 482/8 |
| 2007/0172797 A1 | 7/2007 | Hada et al. |
| 2009/0062627 A1 | 3/2009 | Younger |
| 2009/0069722 A1 | 3/2009 | Flaction et al. |
| 2010/0204615 A1 * | 8/2010 | Kyle et al. ..................... 600/595 |

FOREIGN PATENT DOCUMENTS

| | | |
|---|---|---|
| DE | 102004013997 A1 | 10/2005 |
| EP | 1834583 A1 | 9/2007 |
| GB | 2422790 A | 8/2006 |
| GB | 2447915 A | 10/2008 |
| JP | 2006320533 A | 11/2006 |
| WO | WO 03/032826 | 4/2003 |
| WO | 2005055815 A2 | 6/2005 |
| WO | WO 2005/074795 | 8/2005 |
| WO | 2007036611 A1 | 4/2007 |
| WO | 2007107491 A1 | 9/2007 |
| WO | 2009024600 A1 | 2/2009 |

* cited by examiner

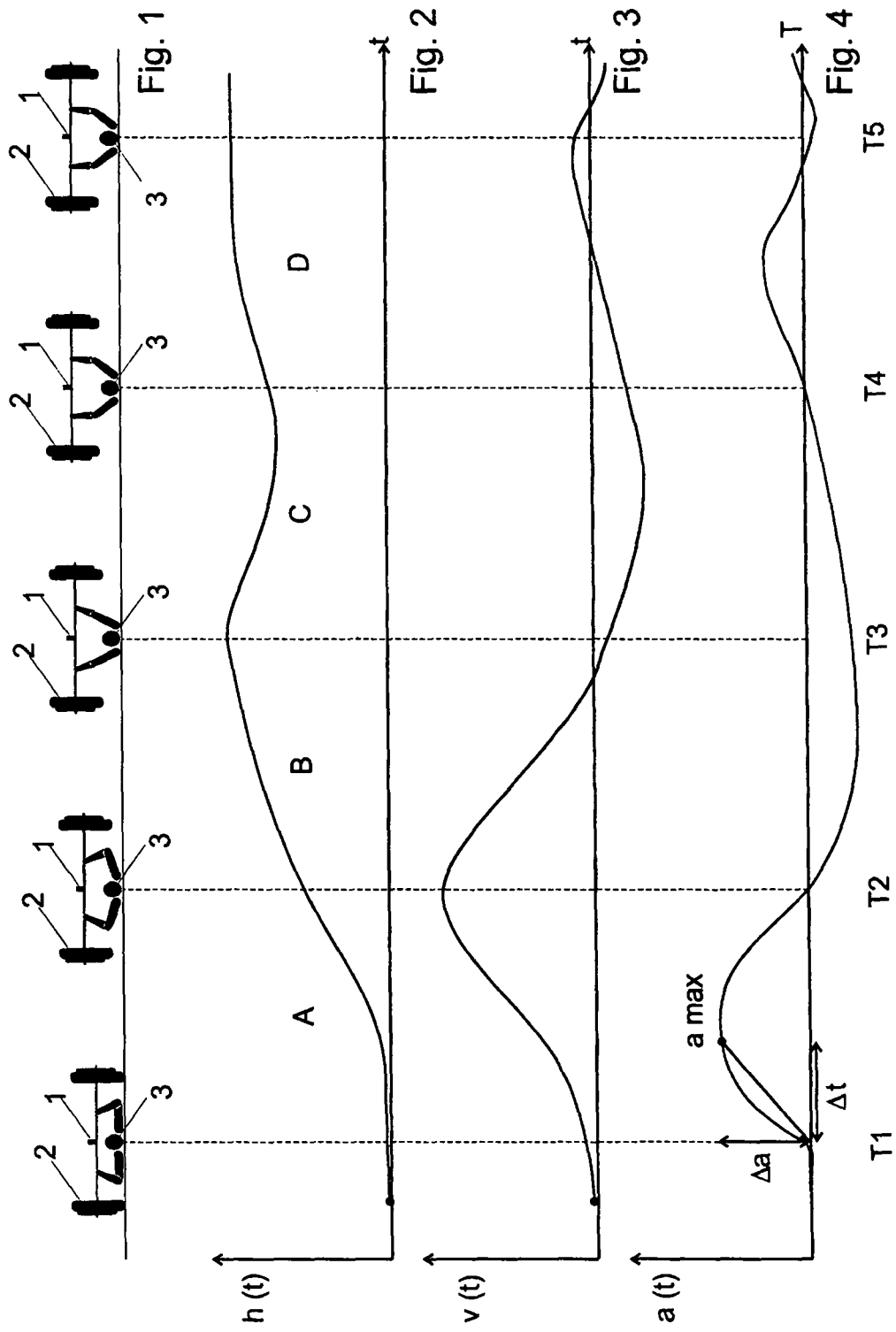

METHOD AND DEVICE FOR ASSESSING MUSCULAR CAPACITIES OF ATHLETES USING SHORT TESTS

The present invention is a continuation of International Application PCT-EP 2007-052413 filed on Mar. 14, 2007 and published under the number WO 07/107,491, the content of which is incorporated here by reference. This application claims the priority of European Patent Application EP07111352, filed on Mar. 17, 2006 and published under the number EP1834583, the content of which is incorporated here by reference.

TECHNICAL FIELD

The present invention relates to the field of methods and devices for evaluating muscular capacity, especially for sport and for rehabilitation. The present invention relates in particular to devices for evaluating muscular physiological parameters, for example muscular power and force, these being based on acceleration measurements.

PRIOR ART

Performance measurement apparatus is being increasingly used for the training of athletes and for rehabilitation after an accident. For example in cardiovascular training (jogging, cycling, etc.), the use of heartbeat meters ("pulsometers") and pedometers has grown substantially in recent years. Such portable apparatus takes measurements during exertion, enabling the athlete to adapt the training using objective data. The measured quantities delivered typically indicate the heartbeat rate, the distance traveled, the duration of training, the average or maximum speed, etc. However, they do not provide any direct measurement of the muscular power of the athlete or of a muscular chain of the athlete.

U.S. Pat. No. 5,788,655 (Omron) describes an apparatus intended to be fixed to the body and provided with an accelerometer and an LCD display. The apparatus permanently measures the movements of the wearer in order to determine his level of physical activity and other metabolism-dependent quantities, for example the daily calorie consumption of the user. This type of apparatus is useful for measuring the level of sedentariness of patients more objectively. However, it is unsuitable for muscular training and for measuring brief exertions, and is unable to determine for example the maximum power of an athlete's muscle group.

WO 2005/074795 (Nokia) describes a measurement terminal provided with an accelerometer, the terminal being attached to the body of an athlete. The measurement data is evaluated so as to provide a quantity representative of the intensity of exertion delivered. Again, the objective is to determine the level of activity over a long period, for example a day or a week.

WO 03/032826 (Philips) describes a similar system, provided with a three-axis accelerometer for determining the level of physical activity of a patient. The proposed device displays quantities such as the daily metabolic rate, the daily energy expenditure or the energy expenditure induced by exercise. This apparatus is therefore useful for measuring accelerations over a period of several hours, or even several days.

The devices of the type described above are therefore suitable essentially for measuring activity during lengthy exercising, for example over the course of a jogging session, a badminton match or an ordinary day. There are also quite similar devices for detecting falls by the aged, the time that they spend sitting down, standing up or lying down, etc.

However, there is also a need to measure parameters during brief or very brief muscular exertions. For example, muscular training and measurement of muscular capacity of athletes often involve very short movements, for example a single lift of a weight on a muscle-development machine, or a single jump. The sampling frequency employed by the above devices does not generally allow them to be used for measuring kinematic parameters over so brief an exertion. Moreover, the data calculated from the measured accelerations are of little interest for short exertions. For example, it is of little interest to know the amount of calories burnt off during a single movement. However, there is a need for apparatus suitable in particular for muscle development, enabling for example the increase in force or power of a muscle or muscle group being exercised to be measured.

Already known in the prior art are certain measurement devices specifically intended for training and for measurement of brief movements. For example, U.S. Pat. No. 5,474,083 describes a system intended for monitoring weightlifting movements by a patient. The system employs electrodes for measuring the activity of the patient's muscles during the movement and also a weight movement detector. An alarm is triggered in the event of an inappropriate movement. This system is useful for preventing accidents caused by lifting weights incorrectly or for training people to lift weights without hurting themselves. However, it is inappropriate for measuring the muscular performance of a sportsman. Moreover, the use of electrodes makes it not very practical to use.

U.S. Pat. No. 6,397,151 describes a wristwatch device comprising an accelerometer for measuring a sequence of accelerations of the forearm during a blow in a martial arts sport. The force exerted is then calculated. The accelerometer measures an acceleration along a single axis, which must be perfectly aligned with the direction of movement of the forearm. If the wristwatch device moves during the blow, the accelerometer measures only the component of the force along the direction of the accelerometer.

US 2004/134274 describes a device for measuring muscular force. The device includes an inclinometer for measuring its angle of inclination and for obtaining the force along a chosen direction. Inclinometers are expensive and sensitive mechanical devices.

U.S. Pat. No. 6,148,280 (Virtual Technologies) describes a device provided with accelerometers and gyroscopes placed over the entire body of an athlete. The data delivered by several sensors is transmitted to a personal computer, which enables the trajectory and other characteristics of the movement to be analyzed. This system is complex, as it employs several sensors, including expensive goniometers, which are relatively fragile. Connecting the sensors together and to the external computer makes the device expensive and awkward to install. It is suitable for precise movement training, for example a golf swing, but does not allow direct determination of the muscular capacity developed by the sportsman during this movement.

DE 446302 describes an accelerometer used in combat sports to measure the acceleration of the striking surface. The apparatus is not portable and is suitable only for combat sports, such as boxing, karate, etc. An external computer has to be employed in order for the measurement results to be evaluated and displayed.

Other devices based on accelerometers and gyroscopes exist, enabling for example the trajectory of a golf swing to be monitored so as to improve the movement. U.S. Pat. No. 5,056,783 describes for example a baseball bat provided with a three-axis accelerometer in order to specify the movement of the bat in space. This type of device delivers a large amount of data, for example the position and speed of the sensor at each instant, often requiring a large screen or an external device to display this data. However, such devices are unable to calculate and immediately display thereon one or more quantities representative of the athlete's muscular capacity.

BRIEF DESCRIPTION OF THE INVENTION

The aim of the present invention is to provide a measurement method and a measurement device enabling the muscular capacity of athletes to be evaluated. The aim of the present invention is to propose a rapid test with an instrument which is simple to use, is autonomous and inexpensive, and capable of immediately delivering data representative of muscle-related qualities of athletes, for example their explosive power, power, muscle relaxation, etc.

One object of the present invention is to provide a sports performance measurement apparatus specifically intended for training and for muscle rehabilitation, involving for example known muscular tests such as jumping or weightlifting tests. In particular, the device must enable relaxation, explosive power and force enhancement (FE) of athletes to be evaluated by means of brief noninvasive tests.

According to the invention, these objectives are achieved in particular by means of a method of evaluating the muscular capacity of athletes using brief tests, such as lifts and/or jumps, comprising the following steps:
  a removable and electrically autonomous measurement device is fastened to a weight that moves during the test, said measurement device being based on a three-axis accelerometer;
  a sequence of successive accelerations of said weight is determined during said test; and
  at the end of said test, at least one quantity representative of said muscular capacity, which is determined from said sequence of accelerations, is indicated on said display.

The muscular capacity may be calculated and displayed at the end of the test, for example in the form of the maximum power, the force enhancement, etc.

The three-axis accelerometer is used to determine the vertical gravity direction, and therefore to obtain the direction of the acceleration along this direction or along any chosen direction corresponding preferably to the direction of displacement of a weight. In a preferred embodiment, the quantity representative of the muscular capacity is determined from a sequence of accelerations along a single axis, for example along the vertical axis during a vertical jump, or along the axis of displacement of the weight. The vertical direction and the orientation of the accelerometer in space are preferably determined in advance, for example during a calibration phase, during which the accelerometer must be kept stationary. Visual and/or audible signals may be emitted during this calibration phase so as to ask the user to keep the accelerometer stationary and oriented as at the start of the exercise.

The device is suitable for measuring acceleration as a function of time and for evaluating the results, for example during the execution of the following tests:
  a weight lift;
  a squat jump and/or countermovement jump;
  a drop jump.

Other tests, including core (abdominals) training tests, bench press tests, plyometric tests, etc., may be employed.

The calculation of the displayed quantities takes into account the a priori knowledge of the form of the acceleration function during these standardized muscular tests. The device uses this prior knowledge to determine quantities that a generic device would be unable to measure. For example, the device of the invention may, in one embodiment, decompose a movement into key phases and calculate the maximum power during one particular phase. For example, a jump may comprise a muscle extension phase followed by a flexion phase. The device is able to segment the measured data so as to determine the start and end of these two phases, and then to calculate for example the power during extension and the maximum rate during flexion.

Typically, the device must be capable of acquiring acceleration data along three axes, at least every 100th of a second, during a brief exertion, i.e. an exertion lasting typically less than 10 seconds, but possibly lasting up to several minutes.

The use of a three-axis accelerometer enables the acceleration along any direction to be calculated, especially along the weight displacement direction, for example the vertical direction in a jump. In a preferred embodiment, only a sequence of accelerations along this preferential direction is used to calculate the quantities displayed.

BRIEF DESCRIPTION OF THE DRAWINGS

Exemplary embodiments of the invention are indicated in the description illustrated by the appended figures in which:

FIG. 1 illustrates schematically various movement phases of an athlete during a weight lift of the "bench press" type;

FIG. 2 illustrates the height of the weight lifted as a function of time (h(t)) during the bench press exercise illustrated in FIG. 1;

FIG. 3 illustrates the speed of the weight lifted as a function of time (v(t)) during the bench press exercise illustrated in FIG. 1;

FIG. 4 illustrates the acceleration of the weight lifted as a function of time (a(t)) during the bench press exercise illustrated in FIG. 1;

EXEMPLARY EMBODIMENTS OF THE INVENTION

FIGS. 1 to 4 illustrate the change in various kinematic parameters during a weightlifting movement of the bench press type. This movement, widely used in muscle development, consists in lifting a weight 2 with both arms, starting from a position in which one's back is lying on a bench. The weight is lifted as high as possible, combining adduction of the shoulder and extension of the elbow. FIG. 1 illustrates five key instants during the test. The test starts at T1, in the initial position illustrated in the first image on the left of FIG. 1. The weight is at its lowest point, the athlete's elbows 3 being bent.

During phase A, between the instants T1 and T2, the athlete 3 lifts the weight, the velocity of which steadily increases, as indicated in FIGS. 2 to 4. The thrust force deployed during this phase is a maximum and the arms are extended.

During phase B, between the instants T2 and T3, the thrust continues, but the lift velocity decreases—the acceleration therefore becomes negative, as may be seen in FIG. 4. The weight is at the maximum height at the point T2.

The athlete then relaxes his exertion during phase C between the key instants T3 and T4. The weight is lowered slightly, so that its velocity becomes negative. This step is followed by a stabilization phase D, between the instants T4 and T5, during which the athlete keeps his arms extended, but tends to lower the shoulders. The acceleration undergone by the weight 2 during this phase tends progressively toward 1G (earth's gravitation).

The key instants T1 to T5 may be determined unambiguously from the data a(t), v(t) and h(t). As will be seen, these quantities can be measured during the exertion by means of a device 1 attached to the weight, ideally placed at the center of mass, and will be used to determine and display the muscular capacity of the athlete.

Figure 5:
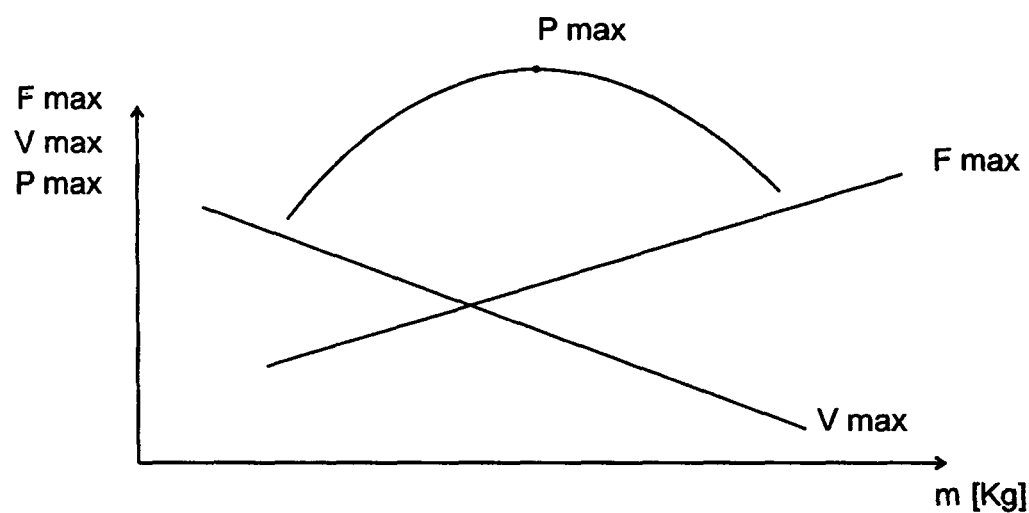
FIG. 5 illustrates the maximum force, the maximum speed and the maximum power that an athlete can deploy as a function of the weight moved.

FIG. 5 illustrates schematically one possible change in the maximum force $F_{max}$, in the maximum velocity $V_{max}$ and in the maximum power $P_{max}$ that an athlete can deploy when lifting a weight of variable mass. The gravitational force (m×g) exerted on the weight deployed increases linearly with the mass of the weight.

In contrast, the force (m×a) exerted by the athlete to pull this mass against gravity depends directly on the force with which the athlete moves the weight. This is because the athlete has the possibility of modifying the acceleration imposed on the weight.

The maximum lift velocity $V_{max}$ tends to decrease with increasing mass of the weight lifted—the athlete lifts light weights more rapidly. The maximum power P deployed by the athlete during the exertion is determined by the formula:

$$P = \frac{dE}{dt} = F \times v = m \times a \times v$$

This formula is valid for the case in which the acceleration and the velocity are parallel to each other, for example during a purely vertical movement. In the case of nonparallel vectors, the calculation must be carried out vectorially.

The maximum power $P_{max}$ during the exertion generally passes through an optimum for a given value of m. A very heavy bar for an athlete will engage an athlete essentially in opposing stresses, i.e. for opposing the gravitational force mg, and little in acceleration stresses ma (the bar is raised more slowly). Thus, it may be seen that by knowing the maximum power, as can be obtained by measuring the acceleration and velocity of the weight, it is possible to determine the optimum weight with which the athlete must train in order to maximize the power deployed during the exercise.

Figure 6:
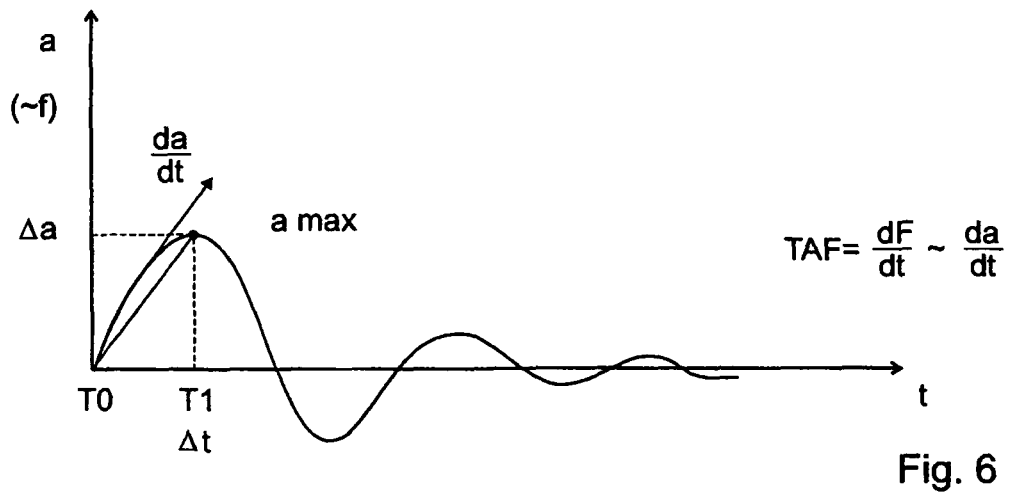
FIG. 6 illustrates the acceleration a(t) as a function of time during an exercise.

FIG. 6 illustrates the change in acceleration a(t) over the course of time during a typical brief exertion, for example a lift or a jump. During the first phase of duration ΔT between the instants T0 and T1, the acceleration increases by Δa. If the weight lifted is constant, the acceleration is proportional to the force. The force enhancement (FE) or explosive power, employed as a sport measurement, is therefore simply proportional to Δa/Δt. The force enhancement is also proportional to the power deployed by the athlete, at least when the distance h traveled by the weight is constant.

It is also possible to determine the instantaneous power P(t) from the value of da/dt at each point on the curve a(t) and to determine the maximum power $P_{max}(t)=\max(P(t))$. This value is however more sensitive to errors and to the measurement noise—smoothing the curve a(t) by means of a noise filter is useful for reducing spurious effects.

Figure 7:
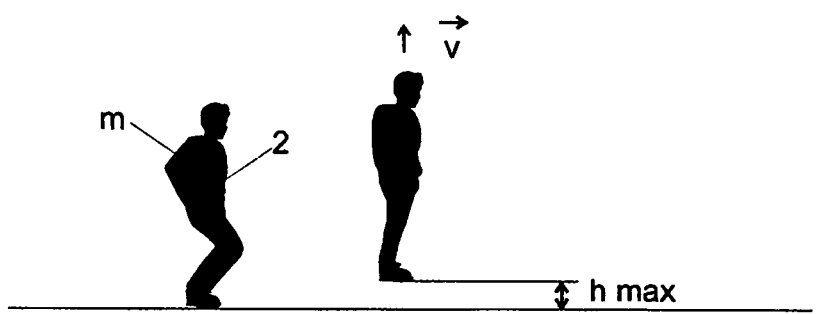
FIG. 7 illustrates a squat jump test.

FIG. 7 illustrates another test used to determine the muscular capacity of an athlete 3. This test, called a "squat jump", is intended in particular to evaluate the relaxation of athletes, in particular dry relaxation, without stretching, and their capability of developing a high force in a very short time (explosive power). The athlete starts with knees bent at 90° and hands on his hips, and then attempts to jump as high as possible. A high initial acceleration is essential to reach a great height.

Figure 8:
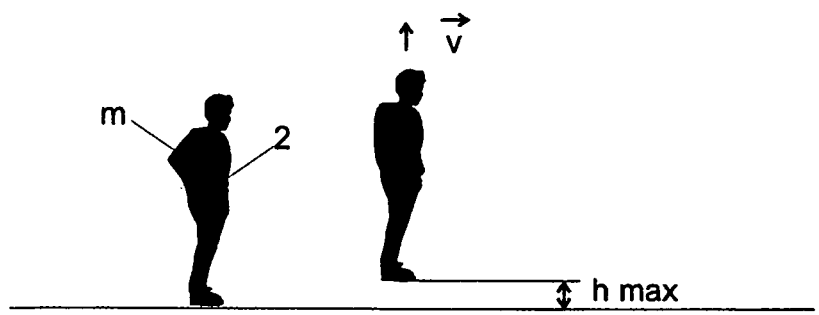
FIG. 8 illustrates a countermovement jump test.

A similar test, called the "countermovement jump", is illustrated in FIG. 8. In this test, the athlete starts in a standing position (legs straight) and is permitted to perform a flexing movement before the extension and jump. The difference between the result obtained in a squat jump and the normally higher height obtained in a countermovement jump depends on the muscular elasticity of the athlete and/or on his capability of developing a greater force during the damping.

Similar tests may be performed in which the athlete is permitted to swing his arms during the jump, in particular so as to check the coordination between arms and legs. The quality of the rebound may be measured by multiple jumps, generally carried out on the spot, using the arms to help. Sometimes squat jump and countermovement jump tests are also carried out with a weight on the athlete's shoulders.

Figure 9:
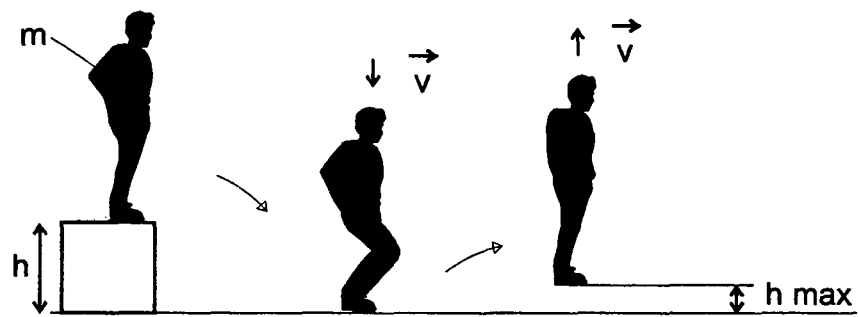
FIG. 9 illustrates a drop jump test.

The drop jump illustrated in FIG. 9 consists of a jump upward after the performer has dropped down from a known height. The impulse is therefore preceded by substantial tensioning which causes the tendons to stretch and different stressing of the muscles. The best athletes thus increase their jumping performance. In general, the test is performed with a 20 cm, 40 cm, 60 cm and 80 cm drop in order to determine the correct working height for each subject.

The jumps mentioned above may be decomposed into distinct phases, separated by key instants. Typically, a squat jump comprises the following phases: start, call, impulse, flight, contact, bounce damping, end.

The above tests may be repeated, for example by performing a series of 10 jumps or 20 lifts, so as to measure for example the change in muscular performance and fatigue resistance of the athlete. One method of use and/or indications on the display of the device preferably indicate the number of tests to be performed. The device can then, depending on the test, perform calculations based either on the average of the successive tests in a series, or on the best test or tests in the series, or on certain predetermined tests in the series, for example by eliminating the first and/or last one(s).

It is also possible to carry out muscle asymmetry measurements, on the arms or the legs, for example by firstly performing a lift with the left arm or the left leg and then with the corresponding right limb. Finally, certain tests enable imbalances between muscles or groups of muscles to be measured, for example a difference in abnormal force between biceps and triceps. These various tests involve several consecutive measurements, which can be stored in memory and then compared with one another. The result of the comparison may be displayed, for example in the form of a percentage, for example 20% of the power difference between left leg and right leg. In the prior art, the performance of athletes in the jump tests described above is often determined using a contact mat which starts a timer when the athlete leaves the mat and stops it when he returns to the ground. The suspension time allows the height reached by the athlete to be determined. These devices however are bulky, expensive and enable the desired data to be obtained only indirectly, based on duration measurements.

The small screen of the device does not allow very detailed results calculated to be displayed. In one embodiment, only summarized results are displayed on the device, for example the maximum power. More detailed results, including for example the sequence of acceleration values along the weight movement direction, or along any other direction, may be displayed and processed by connecting the device to an external computer, for example via a USB connection or the like.

According to the method of the invention, a more significant measurement is obtained by linking the athlete 3 to a device 1 provided with a three-axis accelerometer, enabling the vertical acceleration of the athlete during the weight lift or the jump to be measured. In general, the three-axis accelerometer enables the component of the acceleration along the weight movement direction to be measured.

Figure 10:
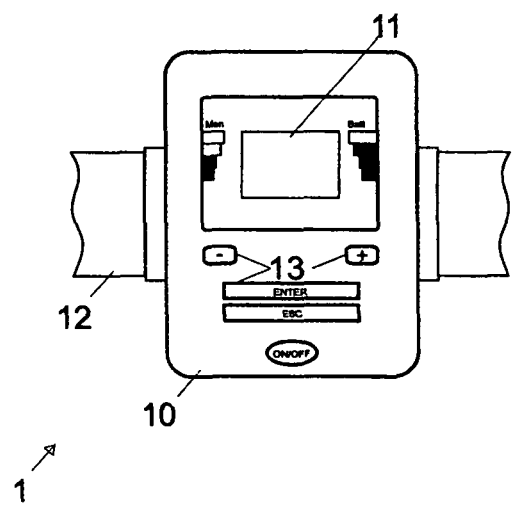
FIG. 10 illustrates a device for evaluating muscular capacity according to the invention.

An example of a suitable device 1 is illustrated in FIG. 10. The device 1 comprises a casing, for example a plastic casing weighing less than 100 grams, preferably less than 50 grams (including the contents), which the athlete can attach, depending on the exercise performed, to his body or to the weight lifted using removable fastening means 12, for example a Velcro strip, a belt, etc. In a variant, the device is simply slipped into a pocket of the garment worn, said pocket being designed for this purpose and being narrow enough to keep the device in position. The fastening means are then simply formed by the shape and the dimensions of the external casing. The casing is preferably sealed and allows use in the open air, being resistant to the athlete's sweat. The fastening means 12 preferably comprise a belt for fastening the device close to the athlete's center of mass, for example to his hips or to his waist, or preferably level with the sacrum, in a slightly inclined position during the exertion. Trials have in fact shown that a belt 12 arranged for supporting the device on the sacrum minimizes the influence of the trunk's movements in the anteroposterior direction. The maximum width of the belt is preferably large, for example greater than 10 centimeters, so that it is held in place better and prevented from being shifted by movements of the skin and flesh over the skeleton.

In a variant, the fastening means enable the device to be fastened to an existing belt. However, it is essential to make sure that a belt is used that does not move during exercises. Fastening the device to one's wrist is however ill-suited for most muscle development tests, especially the tests described above, because the accelerations of the arms or wrist add to the accelerations of the body and because the wrist does not remain vertical during most of the exertions.

The device further includes a display 11, for example an alphanumeric or matrix liquid-crystal display screen, for displaying control menus, the state of the memory, the state of the battery, and also numerical quantities determined during or after the test. Control members 13, for example buttons and/or members for moving a cursor, make it possible to navigate the menus displayed, to select options to input data and to select the results displayed. In a preferred embodiment, the device has four buttons for navigating the menus, these being placed around a central confirm button.

Figure 11:
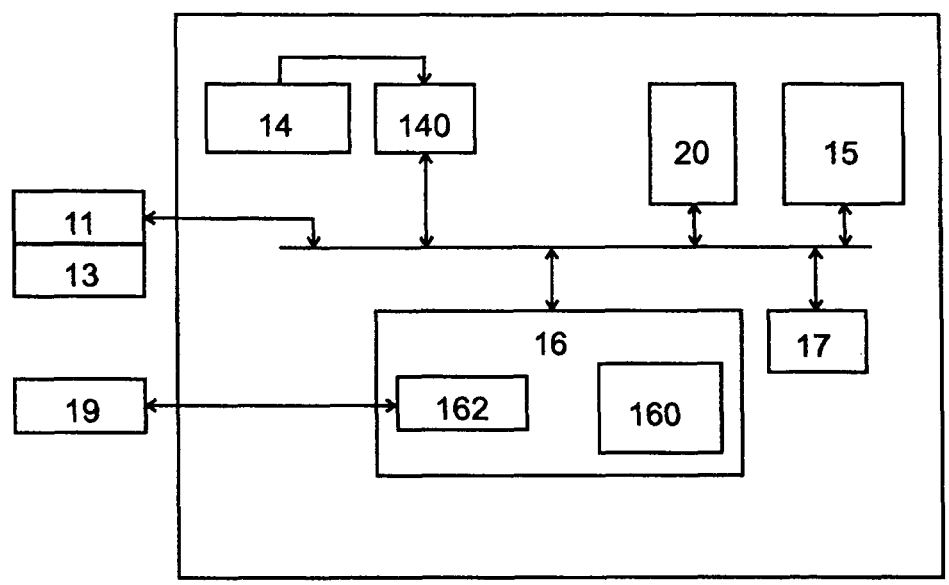
FIG. 11 is a block diagram showing the main electronic components of the device of FIG. 10.

FIG. 11 is a block diagram illustrating the main electronic components of the device 1. Apart from the external members already described in relation to FIG. 10, it includes a three-axis accelerometer 14, for example an accelerometer made in the form of a MEMS component and linked to an analog-digital converter 140, or directly integrating such a converter, so as to deliver sequences of acceleration measurements along three axes. The accelerometer 14 may have one or more preferential axes, offering greater precision, resolution and/or measurement range than in the other axes. This preferential axis will preferably be aligned vertically when the device is in its normal use position, so as to improve the measurement in the vertical direction. The measurement range of the preferential axis or axes is preferably greater than ±8 G, or even ±10 G. The resolution of this axis is preferably greater than 10 or even 12 bits. Preferably, the device does not contain a gyroscope, so as to reduce its cost, its consumption and the volume of data generated. The use of a one-axis gyroscope, or even a three-axis gyroscope, could however be envisioned for certain types of muscular capacity test, or for calibrating the vertical position more certainly.

The device 1 is preferably electrically autonomous, supplied for example by means of a battery 15 or a storage battery that can be recharged, for example via the USB connection 19, or by removing it from the casing. The battery 15 supplies in particular a microprocessor 16 or a microcontroller provided with a RAM and/or EEPROM memory 160. The microprocessor executes a program preferably containing EEPROM, and able to be replaced via one of the interfaces, in order to analyze the measurement data delivered by the accelerometer 14 and to control the display 11 so as to display the desired quantities. An external memory, for example a RAM memory and/or a flash memory, may also be employed. It is also possible to employ interchangeable flash memories, for example of the following types: CompactFlash, SD, MemoryStick, etc., so as to transfer data or programs more rapidly between the device and an external computer.

The device 1 also includes a real-time clock (RTC) 20, in particular for measuring time intervals Δt, and also a buzzer 17 or a loudspeaker for generating alarm signals or other sounds. An input/output module (UART) 162 is used to exchange data between the microprocessor 16 and external devices, for example for reprogramming it or for transmitting measurement results to a personal computer, a mobile telephone or another external data processing device. The module 162 also makes it possible to introduce, at any time, the parameters for new types of test and to determine the way in which the measurement data for these new tests will be exploited, so as to extract the desired representative quantities therefrom.

The module 162 is linked to an interface 19, for example via a USB or mini-USB connection, a wireless interface of the Bluetooth type or the like, etc. The interface 19 is used in particular to recharge the battery, to connect the device to an external computer, to reflash the firmware of the microcontroller and/or to load new tests and new physical exercises into the device.

Figure 12:
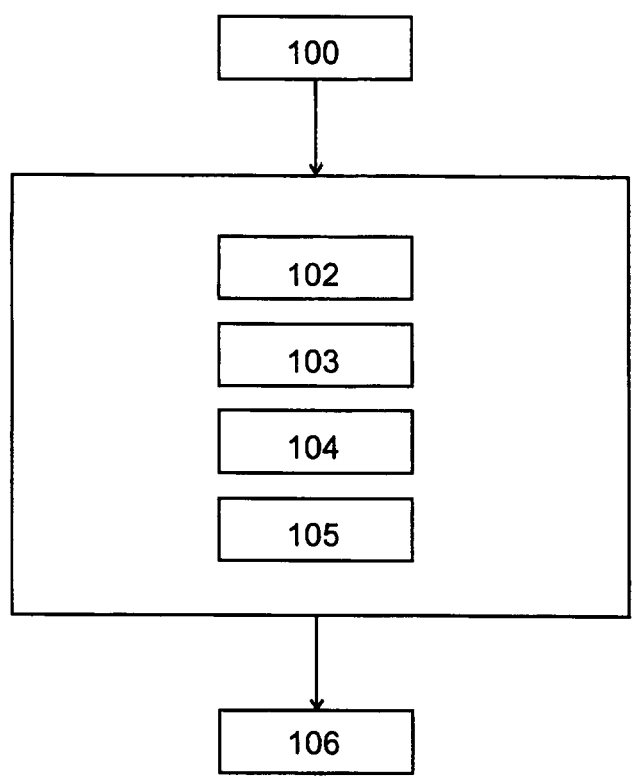
FIG. 12 is a flowchart illustrating the parameterization of the device.

FIG. 12 is a flowchart of the setup program, which is automatically executed when the device is first used, or on request by the user. The setup program is preferably stored in the EEPROM memory 160 and executed by the microprocessor 16. It starts from step 100 before the routine 101 is executed, during which the user has the possibility of inputting information stored permanently in the device. During step 102, the user can input his identification (user ID or username) and possibly an optional password so as to make the device unusable for a possible thief. During step 103, the user can input the preferred measurement units (kg/cm or lb/inch), enabling him to define, in step 103, his weight employed for calculating the force, the work and the power in particular in the jump exercises.

The user can then input the current date and time, which will then be permanently updated by the clock 20.

Other permanent data that can be input at this stage include for example the preferred language of the menus, the type of result displayed, the type of exercise by default, etc.

The numerical data may be input for example by incrementing values by means of + and − keys, or using a numerical keyboard (not shown), or by any other means for inputting data.

Figure 13:
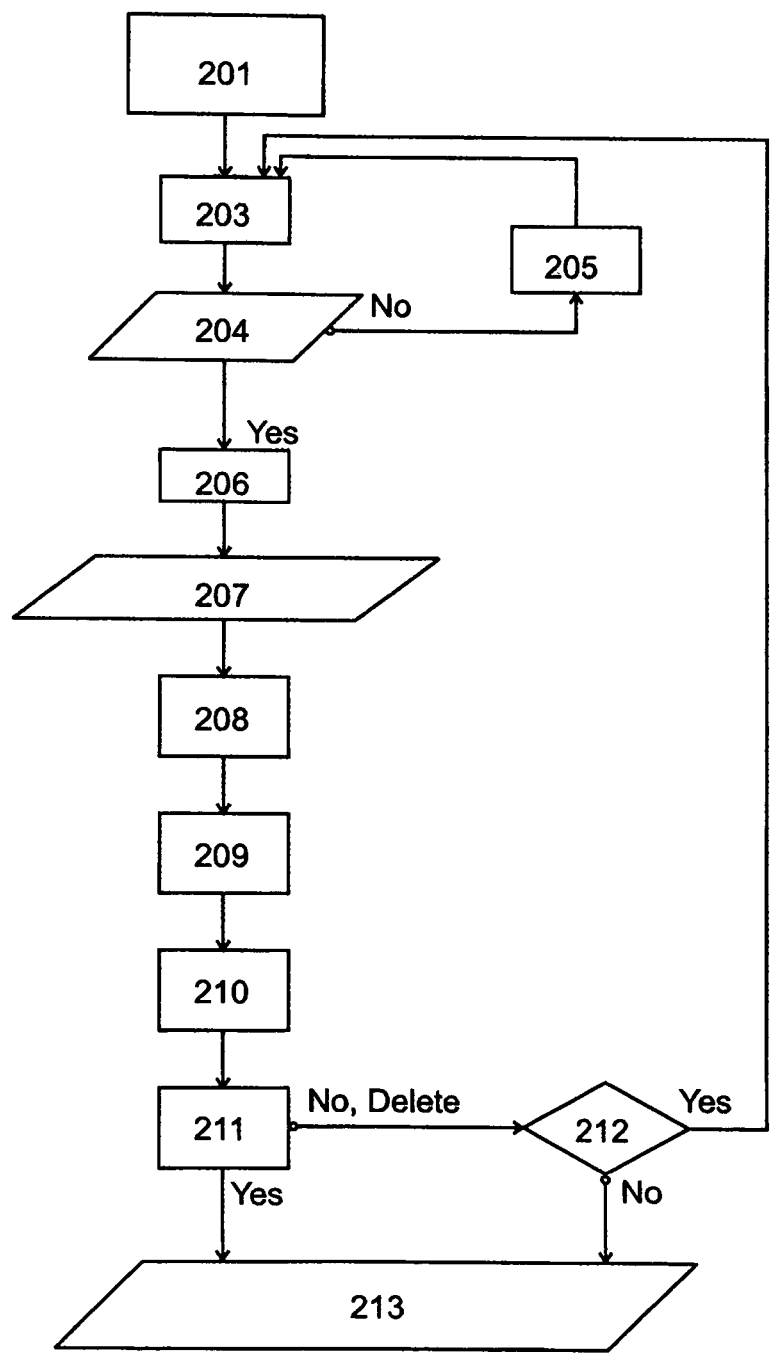
FIG. 13 is a flowchart illustrating the muscular capacity test during the method.

The setup procedure terminates in step 106 and preferably passes immediately into test mode, in order to test the athlete's muscular capacity. The test procedure is illustrated by the flowchart in FIG. 13.

During step 201, the user is invited to choose from a menu the type of test that he desires to perform. This step may be implicit if a default choice is stored in the permanent parameters of the device; it is also possible to propose by default the last test performed. In a preferred variant, the user is invited to choose from the following options, or to confirm a proposed choice from these options:

1. Weight lift
2. Jump (squat or countermovement jump)
3. Drop jump.

The user is also invited to select or confirm parameters that are dependent on the type of test. In the case of a lift, he must thus indicate the mass of the weight in the default unit of the device. In the case of a jump, he may be required to confirm his own weight. In the case of a drop jump, the device will invite him to input or confirm the drop jump height and his own weight.

The actual test starts at step 203, during which the user (the athlete) presses a key, for example an "ENTER" or "START" key (not shown). The device then determines during the calibration step 204 its orientation relative to the vertical. To do this, the athlete is for example invited using a message on the display 11 to stand still for a certain time interval, for example at least 2 seconds. In this position, only gravitation imposes an acceleration on the three-axis accelerometer 14. A reference frame conversion matrix is calculated during this step, so as to convert the measurements along the three axes in a reference frame correctly oriented with respect to the vertical. If the accelerometer detects that the user has moved during the calibration interval 204, the calibration is rejected and a visual and/or audible error message is sent to the display 11 and/or by the buzzer 17. The user is then invited to restart the calibration. The same may occur if the orientation of the apparatus is excessively inclined in relation to the ideal vertical position, for example if the vertical acceleration measurement depends too greatly on the results from the nonpreferential axes of the accelerometer.

Other calibration methods and methods of determining the vertical position may be envisioned, including methods based on an action by the user, who may be invited to place the device on a strictly horizontal surface, or against a vertical wall, or methods involving additional sensors, for example a goniometer for determining the angle or inclination of the athlete's body, a multi-axis gyroscope, a ground satellite receiver of the GPS type, etc.

In the case of successful calibration, an audible beep is emitted during step 206 so as to invite the user to perform the test. The audible signal produced may depend on the test chosen and may furthermore be accompanied by a message on the display 11. The acquisition of a sequence of acceleration data then starts immediately in step 207 and terminates in step 208, after a predetermined duration (for example 10 seconds), when the memory of the device is full or when the user presses a key on the device, for example a key marked "END" or "START/STOP". It is also possible to interrupt the data acquisition automatically, depending on the measured data, for example when the device determines that the athlete has returned to the ground after a jump and that his vertical acceleration is again zero or equal to 1 G.

The acceleration is preferably measured along three axes, at least every 100th of a second or preferably every 2 milliseconds. The three sequences of accelerations are stored in the memory of the microprocessor 16 and then converted into a single sequence of accelerations along the weight movement axis (generally the vertical axis) employing the reference frame conversion matrix determined during calibration.

In a variant, the acceleration data along the three axes is progressively converted by the processor or even directly by logic means on the accelerometer into a sequence of vertical accelerations stored in the memory. A data conversion before storage requires greater computing power, but does enable the size of the storage memory to be reduced or the maximum possible acquisition time for a given memory space to be increased.

At the end of acquisition, or possibly already during acquisition, the processor 16 executes a routine 209 for calculating at least one quantity representative of the athlete's muscular capacity. The calculated quantity and the method of calculation may depend on the type of test selected during step 201. To give an example, the following quantities may be determined:

- the maximum instantaneous power ($\max(P_{inst})$) during the exercise or one particular phase of the exercise (for example during the initial vertical acceleration phase in a jump);
- the maximum power during a time interval ($\Delta T$) of predetermined duration, for example the maximum power during n sampling instants;
- the maximum power during a predetermined phase of the test between two key instants $T_i$, for example the power developed during the thrust, during flexion, or to keep the weight lifted;
- the maximum force enhancement FE (explosive power) during the entire test or during a specified phase of the test;
- the maximum force deployed in the vertical direction during the entire test or during a specified phase of the test;
- the energy expended in the vertical direction during the entire test, or during one phase of the test, for example in joules or in calories;
- the maximum velocity reached during the entire test, or during any phase of the test;
- the maximum height reached in a jump (tests II and III);
- the duration of certain phases of the test, for example the duration of contact with the ground in a drop jump or the duration of flight in a jump;
- the energy efficiency, for example in the form of the ratio of work delivered by the athlete to the kinetic energy of the weight moved;
- the difference between the measured or calculated values after several tests, for example so as to determine fatigue during a repeated exercise, an imbalance between muscles, a left-right asymmetry, an improvement in performance of the athlete, etc. The quantity calculated after a series of exercises may for example be expressed and displayed as a percentage;
- etc.

It is also possible to display several quantities at the end of the test. To reduce the volume and the weight of the device, a digital or alphanumeric display of small size and low consumption, for example a four-line alphanumeric display, will however be employed. Multiple quantities can then be displayed by navigating between several results screens.

The calculation of some of these quantities may involve determining the temporal position of certain key instants and the duration of the period between two key instants. Examples of key instants T1 to T5 are indicated in FIGS. 1 to 4 in the case of a weight lift. In the case of a drop jump, the key instants will for example be the start, the first contact with the ground, the instant when the rebounding athlete leaves the ground, the instant when the maximum height is reached and the instant when the athlete rejoins the ground for the second time, after the rebound. The automatic determination of the key instants based on the acceleration data therefore depends on the type of exercise selected and on the a priori knowledge of the form of the sequence of accelerations, or at least a portion of this sequence. Frequently, the key instants of a movement are the instants during which the acceleration, the velocity or the position pass through a particular point, for example a minimum, a maximum, a passage through zero, a passage through a particular value (for example a 1 G acceleration) or a point of inflection.

It is also possible to determine the phases from which the displayed quantities are determined on the basis of the sign of certain values derived from the acceleration. For example, it is possible to choose to determine the maximum acceleration of all instants during which the velocity is positive, i.e. directed upwardly. The determination of the key instants and of the phases of the movement may also depend on the acceleration data along the nonvertical directions.

The key instants and/or the duration between two key instants ("key duration") may also be displayed at the end of the test as an additional quantity representative of the athlete's muscular capacity.

The measurement may for example be refused if the form of the acceleration sequence obtained does not correspond to the expected model according to the type of test selected and if the measurement does not enable the desired quantities to be obtained. In this case, a visual and/or audible error signal is preferably issued, to invite the athlete to restart the test.

At the end of a conclusive test, one or more of the above quantities are immediately displayed during step 210 on the display 11. Several items of data may be displayed on several lines or on several screens, between which the user can navigate. Calculated quantities may also be stored in the device, for comparison with quantities calculated during other tests.

The user is then invited to validate the test during step 211, for example by pressing an "ENTER" or "OK" key. If he refuses to validate the test, he is invited during step 212 to restart, by returning to step 203, or to interrupt the test, passing directly to step 213. The program passes directly to step 213 when the user validates the results.

During step 213, the results of the validated tests are stored in a semi-permanent memory 160, preferably associating them with the user's identification, the date and time of the test and an identification of the test type. In a first variant, suitable for devices having a large memory, the entire sequence of acceleration data along an axis, or even along all three axes, is stored in memory.

This variant makes it possible for other quantities to be subsequently calculated from this sequence, or to transfer it via the interface 162 and 19 to an external processing unit (PC, PDA, mobile telephone, etc.) for subsequent exploitation, or to calculate and display other quantities and other graphs. The transfer can be carried out automatically as soon as a connection is established with an external device, or by selecting a command in a menu or by another deliberate action by the user of the device 1.

A software application may be loaded into and executed in the external device so as to calculate other quantities, to represent them differently or to extract therefrom information which is more complete than the basic information immediately displayed on the device. The software enables for example quantities to be displayed in graph form or to see them in relation to previous measurements on the same athlete, or on other athletes, or with the objectives of a training program, which may be downloaded from the Internet. This application may also make customized training suggestions, depending on the measurement results for each athlete and taking into account the athlete's progress at several dated tests. The training program proposed may take into account the results obtained during various tests and at different dates.

The software also preferably makes it possible to classify or order various test results using the metadata transmitted by the device, including the date and time of the test, the athlete's identification, identification of the type of test and possible identification of the device employed, and/or using additional data input by the operator in order to classify and group the results.

The previous tests, which are no longer relevant or have been transferred to the external processing unit, may preferably be erased from the memory of the device 1, either automatically during transfer or storage of new results, or by an explicit command input by the user.

In the above method, the acquisition of a new series of accelerations is repeated in each test, for example at each jump or each lift. However, a test is often performed several times in succession with only the best result taken into account. For example, many sports trainers recommend measuring the best squat jump, i.e. the best jump from a series of typically 3 jumps during a brief period. If the memory of the device so allows, it is possible to program the device so as to input, during a single acquisition, the data from several consecutive tests. The device can then be programmed to distinguish the three jumps during the measurement sequence and for example to determine automatically the best one. This type of test also makes it possible to determine, using a single sequence of accelerations, the fatigue or, on the contrary, the increase in relaxation between closely spaced consecutive tests, and thus to display other useful information relating to the athlete's muscle development.

The present invention also relates to a system comprising a measurement device 1, as described above, linked to a data processing medium, comprising a computer program for the external unit, such as a computer, PDA or telephone. The data processing medium may consist of a CD-ROM, a semi-permanent memory (flash, EEPROM, etc.), a hard disk, etc. The computer program executed makes it possible, as indicated above, to communicate with the measurement device 1 and to perform additional calculations and to display additional information based on the data received.

The invention claimed is:

1. A method of evaluating muscular physiological parameters of an athlete using a test, comprising:
   fastening a removable and electrically autonomous measurement device to a weight of known mass, said measurement device comprising a three-axis accelerometer;
   having said athlete move said measurement device and the weight during said test;
   converting a sequence of accelerations along three axes, delivered by said three-axis accelerometer, into a sequence of successive accelerations along a direction of a movement of the weight;
   determining the sequence of successive accelerations of said weight during said test;

decomposing the movement into key phases so as to determine the start and end of a key phase and calculate a maximum power during a predetermined key phase;

determining based on the calculated maximum power an optimum weight with which the athlete must train to maximize power deployed during an exercise;

automatically determining at least one key instant or key phase of the test from said sequence of accelerations based on a priori knowledge of a form of at least one portion of said sequence of accelerations;

determining at least one quantity representative of said muscular physiological parameters in said at least one key instant or during said key phase based on said priori knowledge of a form of at least one portion of said sequence of accelerations; and immediately at the end of said test, indicating the at least one quantity representative of said muscular physiological parameters on a display of the device.

2. The method of claim 1, wherein said at least one indicated quantity comprises at least one quantity proportional to the maximum power deployed by said athlete during the test.

3. The method of claim 1, wherein the maximum power being an instantaneous maximum power.

4. The method of claim 1, wherein the maximum power being a maximum power during a time interval of predetermined duration corresponding to several sampling instants.

5. The method of claim 1, wherein said maximum power being a maximum power during a time interval between two key instants of the test.

6. The method of claim 1, further comprising automatically determining at least one of one key instant, and a key duration of the test from said sequence of accelerations, wherein said at least one indicated quantity being determined by taking into account at least one of said key instant and said key duration.

7. The method of claim 6, wherein said key instant (Ti) or said key duration is displayed on said display.

8. The method of claim 1, further comprising a calculation step and a display step for calculating and displaying, after said test, a maximum force enhancement.

9. The method of claim 1, wherein said at least one indicated quantity comprises at least one quantity proportional to a maximum velocity of said weight during the test.

10. The method of claim 1, wherein a sequence of accelerations and/or data calculated from the sequence of accelerations are transmitted to an external processing device for calculating and displaying quantities or graphs representative of said muscular physiological parameters.

11. The method of claim 1 further comprising determining a vertical direction using a plurality of indications provided by said three-axis accelerometer.

12. The method of claim 1, wherein said test is a weight lift, further comprising
inputting a parameter proportional to the weight lifted into said device, wherein said device is removably fitted so as to move with said weight,
determining a vertical direction before the lift on the basis of indications from said accelerometer at rest,
wherein said at least one indicated quantity estimates the athlete's power.

13. The method of claim 1, wherein the duration of said test is less than 10 seconds, and wherein said sequence of accelerations is measured at least every 100th of a second.

14. A method of evaluating muscular physiological parameters of an athlete using short tests, comprising:
fastening a removable and electrically autonomous measurement device to a weight of known mass that is moved by the athlete during the tests, said measurement device comprising a three-axis accelerometer;

having said athlete move said weight of known mass during the tests;

converting a sequence of accelerations along three axes, delivered by said three-axis accelerometer, into a sequence of successive accelerations along a direction of a movement of the weight;

determining the successive sequence of accelerations of said weight during said tests;

decomposing the movement into key phases so as to determine the start and end of a key phase and calculate a maximum power during a predetermined key phase;

determining based on the calculated maximum power an optimum weight with which the athlete must train to maximize power deployed during an exercise;

automatically determining at least one key instant or key phase of the tests from said sequence of accelerations based on a priori knowledge of a form of at least one portion of said sequence of accelerations;

determining a quantity representative of said muscular physiological parameters in said at least one key instant or during said key phase based on said a priori knowledge of a form of at least one portion of the sequence of accelerations along a direction of movement of said weight; and displaying said quantity.

15. A test device, comprising:

removable fastening means for fastening said test device to a movable weight of known mass;

an autonomous electrical power supply;

a display;

a three-axis accelerometer for delivering a sequence of accelerations of at least 100 measurements per second over a duration between 1 and 10 seconds along a direction of movement of said weight; and data processing device configured to:
decompose the movement into key phases so as to determine the start and end of a key phase and calculate a maximum power during a predetermined key phase;

determining based on the calculated maximum power an optimum weight with which the athlete must train to maximize power deployed during an exercise;

automatically determining at least one quantity representative of the muscular capacity of the athlete during each key phase; and displaying the at least one quantity on said display.

16. The test device of claim 15, further comprising removable means for linking to a computer, a PDA and/or an external computer.

17. The test device of claim 15, further comprising means for selecting a type of exercise performed from a list of several exercises.

18. The test device of claim 15, wherein said removable fastening means are capable of fastening said device to the athlete's waist and/or trunk.

19. The test device of claim 15, wherein said removable fastening means include a hook and loop fastener.

20. The test device of claim 15, wherein said removable fastening means being configured for aligning vertically when the device is in its normal use position to improve a measurement in a vertical direction.

21. A test device to be fastened to a movable weight, comprising:
   a display;
   a three-axis accelerometer configured for delivering a sequence of accelerations along an axis of movement of the movable weight; and
   a microprocessor programmed to allow selection of a type of an exercise to be performed by an athlete from a list of exercises, wherein the microprocessor is configured for:
   decomposing the movement into key phases to determine the start and end of a key phase and calculate a maximum power during a predetermined key phase;
   determining based on the calculated maximum power an optimum weight with which the athlete must train to maximize power deployed during an exercise;
   automatically determining at least one quantity representative of the athlete's muscular capacity during each key phase and;
   displaying the at least one quantity on said display.

22. A system comprising a device as claimed in claim 21 and a data processing storage medium comprising a computer program to be executed by an external processing unit for displaying additional quantities measured by said device.

23. A test device, comprising:
   a hook and loop fastener configured to fasten the test device to a movable weight to be moved by an athlete;
   an autonomous electrical power supply;
   an accelerometer for delivering a sequence of accelerations along the axis of movement of the movable weight;
   a display;
   a microprocessor configured for decomposing the movement into key phases so as to determine the start and end of a key phase and calculate a maximum power during a predetermined key phase and determining based on the calculated maximum power an optimum weight with which the athlete must train to maximize power deployed during an exercise;
   wherein the microprocessor further being programmed to:
   automatically determine at least one key phase of a test from said sequence of accelerations based on a priori knowledge of said sequence of accelerations,
   determine, at least one quantity representative of the athlete's muscular capacity during said key phase, and
   display the at least one quantity on said display.

24. The device of claim 23, further comprising a belt for fastening the device close to the athlete's center of mass.

25. A method of evaluating muscular physiological parameters of an athlete using short tests, comprising:
   fastening a removable and electrically autonomous measurement device to a weight of known mass, said measurement device comprising a three-axis accelerometer;
   having said athlete move said measurement device and the weight of known mass during said tests;
   determining a sequence of successive accelerations of said weight during said tests;
   converting the sequence of accelerations along three axes, delivered by said three-axis accelerometer, into a sequence of accelerations along a direction of movement of said weight;
   decomposing the movement into key phases as to determine the start and end of a key phase and calculate a maximum power during a predetermined key phase;
   determining based on the calculated maximum power an optimum weight with which the athlete must train to maximize power deployed during an exercise;
   determining at least one quantity representative of said muscular physiological parameters based on a priori knowledge of a form of at least one portion of said sequence of accelerations; and
   indicating the at least one quantity representative of said muscular physiological parameters on a display of the device, immediately at the end of said tests.

* * * * *